(12) United States Patent
Machado et al.

(10) Patent No.: US 7,727,188 B2
(45) Date of Patent: Jun. 1, 2010

(54) BALLOON CATHETER WITH POSITIONING POCKET

(75) Inventors: Fidelis Machado, Lawrenceville, NJ (US); Christopher Gregory, Newtown, PA (US)

(73) Assignee: ConvaTec Technologies Inc., Reno, NV (US)

( * ) Notice: Subject to any disclaimer, the term of this patent is extended or adjusted under 35 U.S.C. 154(b) by 404 days.

(21) Appl. No.: 10/738,857

(22) Filed: Dec. 17, 2003

(65) Prior Publication Data

US 2005/0137526 A1    Jun. 23, 2005

(51) Int. Cl.
*A61M 25/10* (2006.01)

(52) U.S. Cl. .................................. 604/103.06

(58) Field of Classification Search .............. 604/27, 604/508, 509, 96.01, 98.01, 101.03, 102.03, 604/103, 103.03, 103.06, 103.07, 103.08, 604/103.11, 102.01, 48, 915, 916, 921; 606/101, 606/104, 106, 114, 115, 191, 192, 194, 197, 606/205–207

See application file for complete search history.

(56) References Cited

U.S. PATENT DOCUMENTS

| | | | | |
|---|---|---|---|---|
| 2,936,760 A | * | 5/1960 | Gants | 604/101.03 |
| 3,841,304 A | * | 10/1974 | Jones | 600/29 |
| 3,866,601 A | * | 2/1975 | Russell | 600/114 |
| 4,516,578 A | | 5/1985 | Shuffield | |
| 5,061,240 A | * | 10/1991 | Cherian | 606/194 |
| 5,108,370 A | * | 4/1992 | Walinsky | 604/102.02 |
| 5,315,747 A | * | 5/1994 | Solar | 29/447 |
| 5,439,445 A | | 8/1995 | Kontos et al. | |
| 5,470,314 A | * | 11/1995 | Walinsky | 604/103.11 |

(Continued)

FOREIGN PATENT DOCUMENTS

WO    WO 99/59667    2/1998

(Continued)

OTHER PUBLICATIONS

"A Unique System Designed to Protect Patients and Practitioners from Fecal Contact and Contamination", Zassi Medical Evolutions—Bowel Management System; 2003; 10 pages.

*Primary Examiner*—Nicholas D Lucchesi
*Assistant Examiner*—Aarti B Berdichevsky
(74) *Attorney, Agent, or Firm*—Stuart E. Krieger

(57) ABSTRACT

The invention relates to a balloon catheter in which the balloon is mounted on the end of the catheter in a manner that creates a recess or pocket between the catheter wall and balloon wall. The recess or pocket opens toward the proximal end of the catheter. The rigid end of an introducer element or finger is received in the recess to attach it to the catheter. The distal end of the catheter, with the end of the introducer element in the recess, is inserted and positioned within the bowel by manipulating the introducer element or finger. After the catheter is properly positioned in the bowel, the introducer element or finger is withdrawn, detaching it from the catheter as the end of the introducer element slides out of the recess and then out of the bowel. The balloon is inflated prior to or after the withdrawal of the introducer element to anchor the end of the catheter in position within the bowel. Since the distal end of the catheter is made entirely of soft, compliant material, no soft tissue damage can occur from use of the device, even when the catheter remains in place within the body over an extended time period.

8 Claims, 2 Drawing Sheets

U.S. PATENT DOCUMENTS

| | | | |
|---|---|---|---|
| 5,549,657 A * | 8/1996 | Stern et al. | 604/537 |
| 5,569,216 A | 10/1996 | Kim | |
| 5,637,091 A | 6/1997 | Hakky et al. | |
| 5,693,036 A | 12/1997 | Kilgour | |
| 5,718,680 A * | 2/1998 | Kraus et al. | 604/509 |
| 5,792,070 A * | 8/1998 | Kauphusman et al. | 600/549 |
| 6,348,039 B1 * | 2/2002 | Flachman et al. | 600/549 |
| 6,364,858 B1 * | 4/2002 | Picha | 604/174 |
| 7,089,942 B1 * | 8/2006 | Grey | 128/207.14 |
| 7,147,627 B2 * | 12/2006 | Kim et al. | 604/327 |
| 2004/0039348 A1 | 2/2004 | Kim et al. | |

FOREIGN PATENT DOCUMENTS

| | | |
|---|---|---|
| WO | WO 01/41858 | 6/2001 |
| WO | WO 02/26293 A1 | 4/2002 |

* cited by examiner

BALLOON CATHETER WITH POSITIONING POCKET

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A "SEQUENCE LISTING", A TABLE, OR A COMPUTER PROGRAM LISTING APPENDIX SUBMITTED ON COMPACT DISC

Not Applicable

BACKGROUND OF THE INVENTION

1. Field of the Invention

The present invention relates to a balloon catheter designed to be introduced into a body cavity, and more particularly to a balloon catheter including a recess or pocket adapted to receive the end of a separate withdrawable rigid element or finger to aid in the introduction and positioning of the balloon carrying catheter end within a body cavity.

2. Description of Prior Art Including Information Disclosed Under 37 CFR 1.97 AND 1.98

Annular inflatable balloons surrounding the distal end of catheters have been used for many years to retain the distal end of a catheter in position in anatomical organs. Such catheters are commonly used for urinary, thorasic and other applications as well as enema delivery. Those devices, commonly called Foley catheters, are every often employed for urinary catheterization.

Because the distal end of the catheter must be inserted into and properly positioned within the anatomy, it must be sufficiently rigid to be manipulated. However, having a rigid part within many body organs can cause distention of the tissue, such as sphincter muscles or delicate vessels, resulting in the loss of muscle tone or tissue integrity over time.

One such system designed to provide bowel management is disclosed in U.S. Pat. No. 5,569,216 issued Oct. 29, 1996 to Jae H. Kim and entitled "Multipurpose Colostomy Device Having Balloons On An End Thereof." The Kim system consists of an elongated flexible catheter, the proximal end of which is detachably connected to a waste collection bag. The distal end of the catheter is designed to be inserted through the rectum or stoma into the bowel of the patient.

The distal end of the Kim catheter includes a resilient portion needed for insertion and positioning of the catheter in the bowel. The distal end of the catheter also carries two inflatable balloons, one balloon being situated within the other balloon. The balloons are separately inflatable to block the distal end of the catheter and to seal the catheter to the rectum or stoma, respectively.

Other known rectal catheters include a catheter with a distal end having a rigid portion which can cause soft tissue damage if it remains in the bowel for an extended period of time. However, the rigidity of the distal end of the catheter is needed to permit the introduction and positioning of the device within the bowel.

One possible way to avoid the potential for soft tissue damage resulting from the use of a rigid portion of the distal end of the catheter, and still provide a means to introduce and position the distal end of the catheter within the bowel, is to utilize a catheter with a distal end made entirely of soft, compliant material and a separate elongated rigid introducer element that attaches to the distal end of the catheter during insertion and positioning and then can be detached from the catheter and withdrawn from the bowel. In this way, insertion and proper positioning of the distal end of the catheter is accomplished without the necessity of leaving a rigid part in the body for an extended time.

However, the use of a separate rigid introducer element raises the issue of how to attach the element to the distal end of the catheter during insertion and positioning of the catheter within the bowel and thereafter to detach the element from the catheter once the distal end of the catheter is properly positioned, thereby permitting the element to be withdrawn from the body, without causing any soft tissue damage.

The present invention is a simple and elegant solution to this problem. It involves mounting the balloon on the end of the catheter in a manner that creates a recess or pocket between the catheter wall and balloon wall. The recess or pocket opens toward the proximal end of the catheter. The rigid end of the introducer element is received in the recess to attach it to the catheter. The distal end of the catheter, with the end of the introducer element in the recess, is inserted and positioned within the bowel by manipulating the introducer element. After the catheter is properly positioned in the bowel, the introducer element is withdrawn, detaching it from the catheter as the end of the introducer element slides out of the recess and then out of the bowel. The balloon is inflated to anchor the end of the catheter in position within the bowel, either before or after the introducer element is withdrawn.

Since the distal end of the catheter is made entirely of soft, compliant material, no soft tissue damage can occur from use of the device, even when it remains in place over an extended time period. This system also allows the tip of the rigid introducer element to lie close to the distal end of the balloon allowing the smooth introduction of the catheter. Once in place with the balloon inflated, the pocket is virtually undetectable under the balloon.

The introducer element may be an elongated rigid part, as described below and illustrated in the drawings. Alternatively, since the finger of the health care professional inserting the catheter is elongated and can be rigid, it may be employed as the introducer, for example, in those situations in which an elongated rigid part designed for introduction of the catheter is not available. Accordingly, the term "element" as used in this patent to describe the means used to introduce the catheter should be understood to include either an elongated rigid part designed for introduction of the catheter or the finger of the health care professional.

It is, therefore, a prime object of the present invention to provide a balloon catheter with a distal end formed entirely of soft, compliant materials that is capable of being inserted and positioned within a body cavity with the aid of a detachable and withdrawable elongated rigid element or finger.

It is another object of the present invention to provide such a balloon catheter with a pocket or recess adapted to receive the end of a separate, elongated rigid element during insertion and positioning within the bowel, and thereafter to permit withdrawal of the element.

It is another object of the present invention to provide a balloon catheter which can be inserted and positioned within a body cavity, and remain in place for an extended period of time, without causing soft tissue damage.

BRIEF SUMMARY OF THE INVENTION

The present invention is a medical appliance in the form of a catheter with a balloon carrying distal end formed entirely of soft, compliant material, and therefore incapable of causing any injury to the soft tissue. The rigid portion of a distal end of the appliance, normally needed for insertion, is embodied in a separate element, designed to be withdrawn after introduction of the catheter in the bowel, thus permitting the entire inserted distal end of the catheter to be soft and compliant so that it cannot damage the tissue.

A pocket or recess is formed in the distal end of the catheter, preferably between the exterior surface of the catheter tube and the balloon wall. The pocket or recess is open towards the proximal end of the catheter. The distal end of the rigid introducer element can be received in the pocket or recess as the element is moved from the proximal end of the catheter tube toward the distal end. Once received in the pocket or recess, the distal end of the catheter and the distal end of the element are attached together and can be manipulated as a unit.

The catheter end is introduced into the body cavity by pushing it and the distal end of the rigid introducer element through the anal sphincter or stoma. The rigid element is manipulated by its proximal end until the balloon is positioned as desired.

Once in position, the catheter and the introducer element are separated. The exposed portion of the catheter tube is held firmly while the introducer element is pulled in the proximal direction. This causes the distal end of the element to slip out of the pocket or recess and separates the element from the catheter. Once the catheter and the introducer element are separated, the introducer element is withdrawn from the body cavity, leaving the distal end of the catheter in place.

In accordance with one aspect of the present invention, a catheter is provided including a tube with a distal end and a proximal end. A recess is formed proximate the distal end of the tube. The recess has an access opening facing the proximal end of the tube.

An inflatable balloon is mounted on the tube, proximate the distal end. The recess is preferably situated between the tube and the balloon.

The recess includes a wall having spaced side edges and a distal edge. The side edges and the distal edge of the recess wall are attached to the tube. The proximal edge of the recess wall remains unattached so as to form an entrance into the recess.

The recess wall extends around a portion of the tube. The distal edge of the recess wall is spaced from the distal end of the tube. Preferably, the recess wall comprises a portion of the balloon.

The balloon is formed by a wall. The recess is defined, in part, by a portion of the balloon wall. That portion of the balloon wall has spaced side edges and a distal edge. The side edges and the distal edge of that portion of the balloon wall are affixed to the tube. The distal edge of that balloon wall portion is spaced from the distal end of the tube.

That portion of the balloon wall has a proximal edge. The proximal edge of that balloon wall portion is situated proximate to the proximal portion of the balloon wall.

In accordance with another aspect of the present invention, a catheter and means for introducing the catheter into a body cavity are provided in combination. The catheter includes a tube with a distal end and a proximal end. A recess is formed in the catheter proximate the distal end of the tube. The recess has an access opening facing the proximal end of the tube. The introducing means includes a rigid element. The rigid element is adapted to be received within the recess, through said access opening.

An inflatable balloon is mounted proximate the distal end of the tube. The recess is preferably situated between the tube and the balloon.

The recess includes a wall having spaced side edges and a distal edge. The side edges and the distal edge of the recess wall are attached to the tube. The proximal edge of the recess wall remains unattached so as to form an entrance into the recess.

The recess wall extends around a portion of the tube. The distal edge of the recess wall is spaced from the distal end of the tube. The recess wall preferably includes a portion of the balloon.

The balloon is formed by a wall. The recess is defined, in part, by a portion of the balloon wall. That portion of the balloon wall has spaced side edges and a distal edge. The side edges and the distal edge of that balloon wall portion are affixed to the tube. The distal edge of that balloon wall portion is spaced from the distal end of the tube.

That portion of the balloon wall also has a proximal edge. The proximal edge of that balloon wall portion is situated proximate to the proximal portion of the balloon wall.

The introducing means includes a handle portion. The rigid element is attached to the handle portion. The rigid element is elongated. A flange is provided extending from the rigid element.

In accordance with another aspect of the present invention, a method is provided for introducing the end of a catheter into a body cavity utilizing an elongated rigid element. The catheter includes a tube with a distal end and a proximal end. A recess is formed proximate the distal end of the tube. The recess has an access opening facing the proximal end of the tube. The method includes the steps of: inserting the end of the rigid element into the recess; manipulating the rigid element in order to introduce the distal end of the tube and the end of the rigid element into the body cavity; and withdrawing the rigid element from the body cavity.

The catheter has an annular balloon mounted proximate to its distal end. The recess is situated between the tube and the balloon.

The rigid element is attached to a handle. The step of manipulating the rigid element includes the step of manipulating the handle. The step of inserting the rigid element includes the step of manipulating the handle. The step of withdrawing the rigid element includes the step of manipulating the handle.

BRIEF DESCRIPTION OF THE SEVERAL VIEWS OF DRAWINGS

To these and to such other objects which may hereinafter appear, the present invention relates to a balloon catheter with positioning pocket, as set forth in detail in the following specification, recited in the annexed claims, taken together with the accompanying drawings, in which like numerals refer to like parts, and in which:

DETAILED DESCRIPTION OF THE INVENTION

Figure 1:
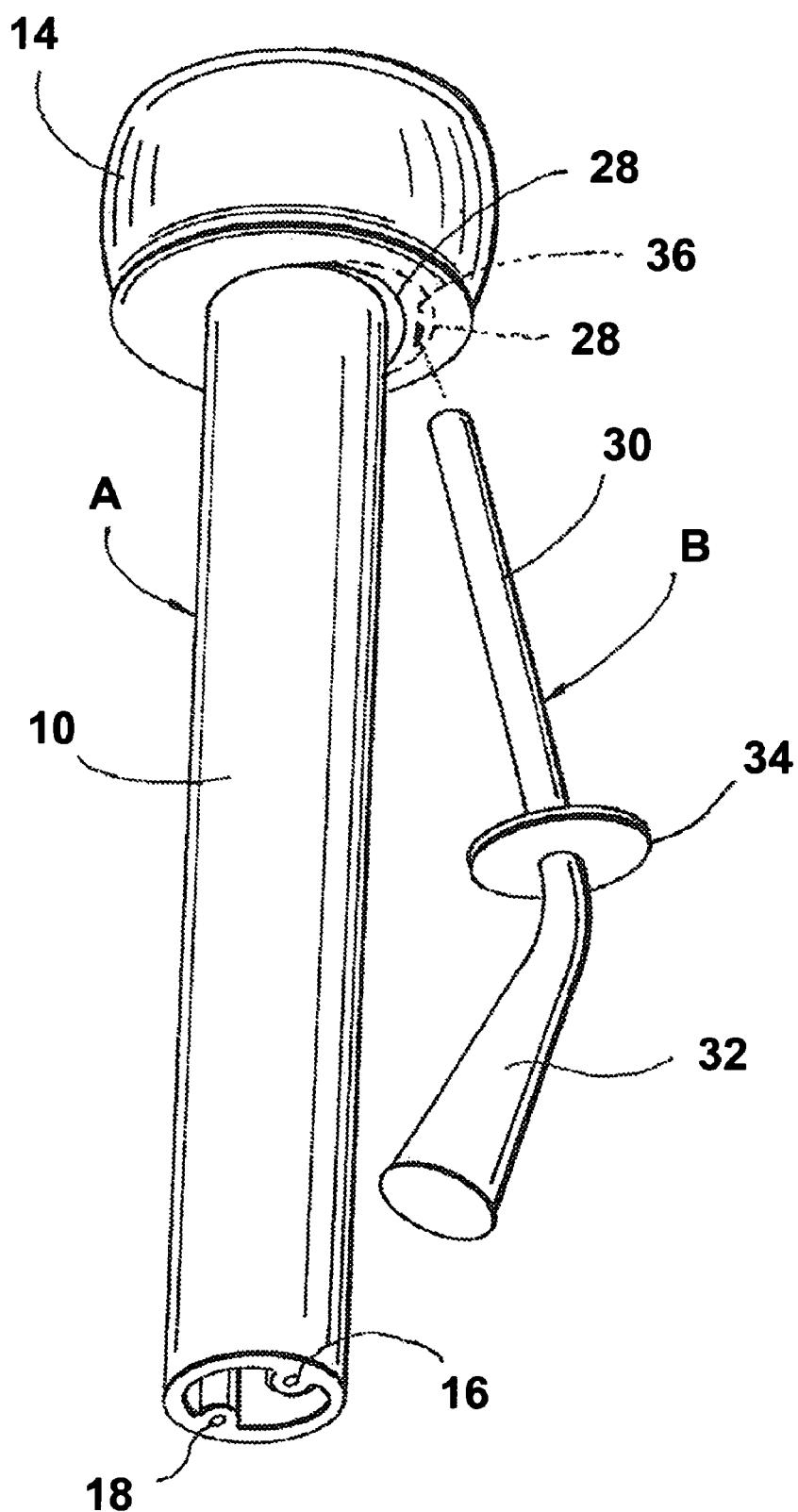
FIG. 1 is a side elevational view of the distal end of the catheter and the introduction element of the present invention, showing the catheter and element prior to attachment.

As is best seen from FIG. 1, the present invention includes a balloon catheter, generally designated A, and a separate introducer element, generally designated B. Catheter A consists of a flexible tube 10 made entirely of soft, compliant material. Tube 10 has a distal end 12 that carries an inflatable balloon 14. Balloon 14 is heat sealed or otherwise affixed to the exterior surface of tube 10. Balloon 14 is also formed entirely from soft, compliant material.

Figure 2:
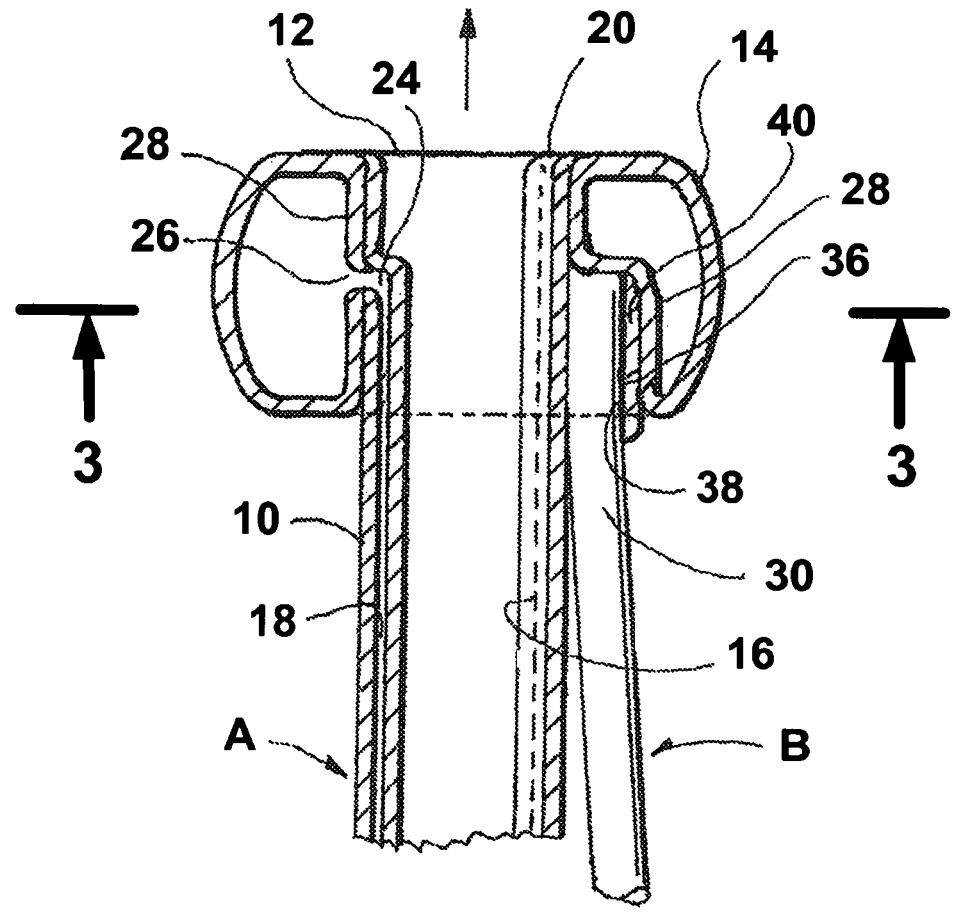
FIG. 2 is a cross-sectional view of the distal end of the catheter with the introducer element attached.
Figure 3:
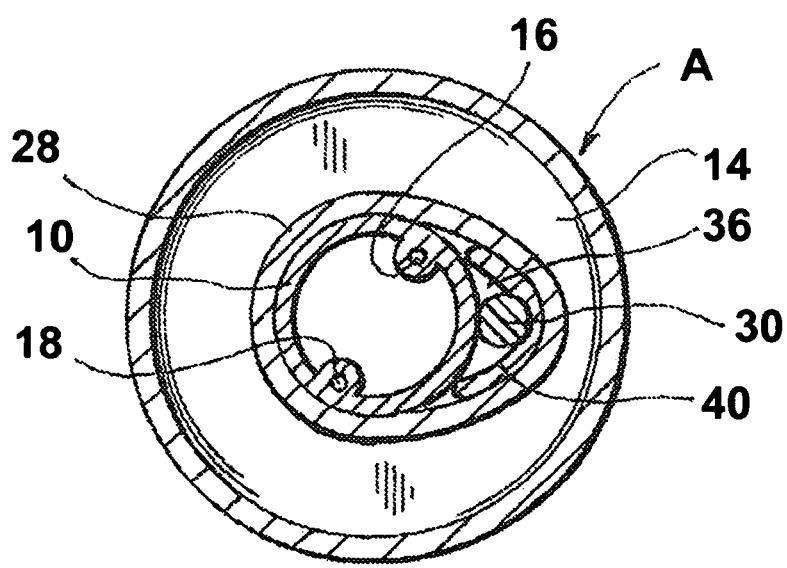
FIG. 3 is a cross-sectional view of the distal end of the catheter taken along line 3-3 of FIG. 2.

The interior surface of tube 10 has two integral lumens 16, 18, best seen in FIGS. 2 and 3. The distal end 20 of lumen 16 terminates at the end 12 of tube 10 so as to permit fluid to be introduced into the bowel once the catheter is in position. The distal end 24 of lumen 18 terminates at opening 26 in the wall 28 of balloon 14. The proximal end of lumen 16 (not shown) is attached to a syringe or other source of inflation fluid that is introduced into balloon 14 through lumen 16 to inflate the balloon after the distal end of catheter tube 12 is in position within the bowel. Lumen 16 will also provide a means of removing the inflation fluid from the balloon, when the catheter is to be extracted from the bowel.

Element B is made rigid material, such as plastic. It consists of an elongated distal end 30 and an integral, angled handle 32. A flange 34 is affixed to the distal end 30, proximate the junction with the handle.

A recess or pocket 36 is formed between the exterior surface of the wall of tube 10 and the interior surface of balloon wall 28 and extends around a portion of the exterior of the tube. Recess 36 can be formed by simply not sealing a portion of balloon wall 28 to the exterior surface of tube 10 such that the side edges and distal edge of the recess are closed and but the proximal edge of the recess remains unattached such that an opening 38 facing the proximal end of tube 10 is formed.

Another way to form recess 36 is to seal the exterior surface of a separate section 40 of tube material to balloon wall 28 before the remainder of balloon wall 28 is sealed to the exterior surface of tube 10. Then the side edges and the distal edge of section 40 are sealed to the exterior surface of tube 10 when the balloon is mounted such that wall 40 extends around a portion of the exterior surface of tube 10. Whether section 40 is used or not, recess 36 is formed with an entrance opening 38 facing the proximal end of tube 10. Access opening 38 of recess 36 permits the distal end 30 of element B to be inserted into and received within the recess, as seen in FIG. 2.

Once the end of the introducer element B is received in recess 36, handle 32 is manipulated to insert and position the distal end 12 of catheter A and the distal end of the introducer element as a unit within the bowel. After the catheter is positioned, the exposed portion of catheter tube 10 is held in one hand while the introducer element is moved towards the proximal end of the catheter by the other hand. That causes the end of the introducer element to slip out of the recess, detaching the introducer element from the catheter so that the introducer element can be withdrawn from the body.

Balloon 14 is inflated to anchor the distal end of the catheter in position within the bowel where it can remain for an extended period of time with causing soft tissue damage. When it comes time to remove the catheter, the balloon is deflated and the distal end of the catheter is easily removed from the bowel.

While the catheter of the present invention is designed for use with an introducer element, as set forth above, it should be understood that instead of the introducer element, a finger could be used. In that instance, the fingertip is received within the recess between the tube and the balloon. The finger is used to insert and position the end of the catheter within the bowel. After the catheter is properly positioned, the finger is withdrawn from the recess and then the body.

It will now be appreciated that the present invention relates to a balloon catheter with a distal end made entirely of soft, compliant material. A recess or pocket is formed between the catheter tube and the balloon that is adapted to receive the end of a rigid elongated introducer element. The distal end of the catheter and the end of the introducer element are then introduced and positioned within the bowel as a unit. After the distal end of the catheter is in position, the introducer element is detached from the catheter and withdrawn from the bowel. This leaves only soft, compliant parts within the body that cannot damage soft tissue even after extended time periods.

While only a single preferred embodiment of the present invention has been disclosed herein for purposes of illustration, it is obvious that many variations and modifications could be made thereto. It is intended to cover all of these variations and modifications which fall within the scope of the present invention, as defined by the following claims:

We claim:

1. A balloon catheter capable of being introduced rectally into the bowel, said balloon catheter comprising a tube with a distal end and a proximal end, an inflatable balloon mounted on said distal end, said tube and balloon being soft and compliant, and a recess proximate to said distal end of said tube between an outer surface of said distal end of the tube and said inflatable balloon, said distal end, balloon and recess being predeterminedly dimensioned to be insertable through the rectum into the bowel, said inflatable balloon being predeterminedly dimensioned when inflated to retain said distal end within the bowel, said recess including an access opening facing said proximal end of said tube, said recess and access opening being predeterminedly dimensioned and oriented to accommodate a finger tip, said access opening and recess being predeterminedly dimensioned so that the finger tip is removably receivable within said recess through said access opening for manipulatably inserting said inflatable balloon into the bowel with the finger tip and remaining in the bowel when the finger tip is removed.

2. The balloon catheter of claim 1 wherein said recess comprises a wall having spaced side edges and a distal edge, said side edges and said distal edge of said recess wall being attached to said tube.

3. The balloon catheter of claim 2 wherein said recess wall extends around a portion of said tube.

4. The balloon catheter of claim 2 wherein said distal edge of said recess wall is spaced from said distal end of said tube.

5. The balloon catheter of claim 2 wherein said recess wall comprises a portion of said balloon.

6. The balloon catheter of claim 5 wherein said balloon is formed by a wall and wherein said recess is defined, in part, by a portion of said balloon wall.

7. The balloon catheter of claim 5 wherein said portion of said balloon wall has spaced side edges and a distal edge and wherein said side edges and said distal edge are affixed to said tube.

8. The balloon catheter of claim 7 wherein said distal edge of said balloon wall portion is spaced from said distal end of said tube wherein said proximal edge of said balloon wall portion is situated proximate to the proximal portion of said balloon wall.

* * * * *